United States Patent [19]

Yahagi et al.

[11] Patent Number: 4,695,640

[45] Date of Patent: Sep. 22, 1987

[54] ADDITION COMPOUND OF FLUORAN COMPOUNDS AND KETONE

[75] Inventors: Masakichi Yahagi, Tokyo; Tetsuo Igaki, Kawagoe; Shinji Yoshinaka, Iwatsuki; Kimiaki Kinoshita, Kitamoto; Morikuni Saito; Toshiyuki Yamashita, both of Tokyo; Morio Nanbu, Fujimi, all of Japan

[73] Assignee: Shin Nisso Kako Co., Ltd., Tokyo, Japan

[21] Appl. No.: 789,950

[22] Filed: Oct. 21, 1985

[30] Foreign Application Priority Data

Oct. 24, 1984 [JP] Japan ................................ 59-223460

[51] Int. Cl.$^4$ ........................................... C07D 407/02
[52] U.S. Cl. .................................... 549/226; 503/221
[58] Field of Search ......................................... 549/226

[56] References Cited

FOREIGN PATENT DOCUMENTS 60719 8/1973 Japan .
109120 10/1974 Japan .
197463 11/1984 Japan .
47068 3/1985 Japan .
2141727 1/1985 United Kingdom .

Primary Examiner—Richard L. Raymond
Attorney, Agent, or Firm—George B. Oujevolk

[57] ABSTRACT

Addition compound of fluoran compound and ketone useful as color former for heat or pressure-sensitive color-developable recording material.

1 Claim, 2 Drawing Figures

ADDITION COMPOUND OF FLUORAN COMPOUNDS AND KETONE

FIELD OF THE INVENTION

This invention relates to a novel addition compound of fluoran compound and ketone and more particularly to a color developable substance with high color developable ability which can be used for the color developable recording material utilizing the heat sensitive or pressure sensitive color development.

DESCRIPTION OF THE PRIOR ART

The high speed of facsimile comunication necessitates the improvement of the color developing rate (color developability) of a color developing dye because most of such high speed comunication is using the heat sensitive recording paper having on the surface thereof the layer containing a color developing dye (hereinafter referred to as "color developing dye" or "color former"), which is ordinarily colorless or light colored and developes color, by the action of an acidic substance and a color developer (the acidic substance) to develop the dye heat sensitively. There is highly desired the improvement of the color developing properties of the dye as well as the improvement of color developer and sensitizer.

As a color developing dye, particularly a black color developing dye, for the heat sensitive recording paper, the fluoran compounds are important. There is desired also the highly improvement of the color developing rate of these fluoran compounds.

On the other hand, a compound of the general formula (I) (hereinafter mentioned) wherein $R_1$ is amino group A (hereinafter mentioned), that is, 3-N-i-butylethylamino-6-methyl-7-phenylaminofluoran (hereinafter referred to as "fluoran compound A") is disclosed in Japanese Patent Pablication (before examination) No. Tokkaisho 59-197463 (1984). A compound of the general formula (I) (hereinafter mentioned) wherein $R_1$ is amino group B (below mentioned), that is, 3-N-methylcyclohexylamino-6-methyl-7-phenylaminofluoran (hereinafter referred to as "fluoran compound B") is disclosed in Japanese Patent Pablication (before examination) No. Tokkaisho 49-109120 (1974). A compounds of the general formula (I) (hereinafter mentioned) wherein $R_1$ is amino group C (below mentioned), that is, 3-N-ethyl-p-toluidino-6-methyl-7-phenylaminofluoran (hereinafter referred to as "fluoran compound C") is disclosed in Japanese Patent Pablication (before examination) No. Tokkaisho 48-60719 (1973). The fluoran compound B and the fluoran compound C have been commercially provided in use for the heat sensitive recording paper and the pressure sensitive copying paper.

The present invention satisfies the above desire and provides the materials having extremely high heat sensitivity as compared to the above mentioned fluoran compounds A, B, and C to be developed as black color.

SUMMARY OF THE INVENTION

The inventors have found that the fluoran compounds having the general formula (I) (hereinafter mentioned) can form the addition compound with ketone and found that the heat sensitive recording paper containing these addition compounds developes the color easily as compared with one containing the fluoran compound not combined with ketone.

Accordingly, it is an object of this invention to provide a novel addition compound with high sensitivity in use for color developing materials such as the heat sensitive recording paper and the pressure sensitive copying paper.

It is another object of the invention is to provide a new type of color former which developes color in high sensitivity.

It is another object of the invention to provide a heat sensitive color developing recording material, which has high sensitivity.

It is another object of the invention to provide a pressure sensitive copying paper, which has high sensitivity.

The foregoing and other objects of the present invention can be attained by the following:

DETAILED DESCRIPTION OF PREFERRED EMBODIMENTS

This invention is a novel addition compound of the fluoran compound having general formula (I) and ketone having general formula (II).

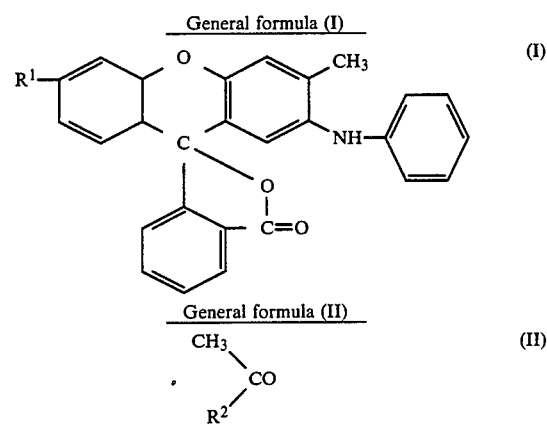

wherein $R_2$ is one of a group of methyl ($CH_3$—) and ethyl ($C_2H_5$—) when $R_1$ represents

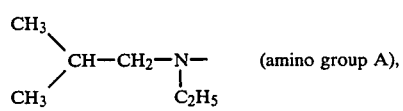

(amino group A), and $R_2$ is methyl ($CH_3$—) when $R_1$ is one of

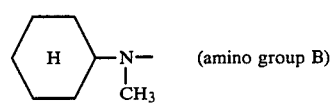

(amino group B)

and

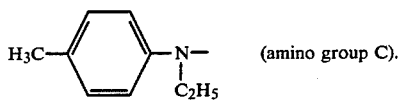 (amino group C).

In accordance with this invention, the novel addition compound can be produced by adding the fluoran compound to the ketone of an appropriate amount, under heating for appropriate period and allowing the resultant to cool, to yield precipitated white crystals by filtering.

The amount of ketone to be used in that which is necessary and sufficient to dissolve completely the fluoran compound as being heated, or may not be enough to dissolve completely the fluoran compound so that a part of the fluoran compound remains undissolved in solution. In the latter case, the remaining fluoran compound will be dissolve in the ketone and change gradually into the addition compound with the passage of heating time. The melting points of the addition compounds of this invention are shown in Table 1 together with the starting fluoran compounds that are not combined with ketone.

The formation of addition compound of fluoran compound and ketone does not occur to all of the fluoran compounds, and there is found high selectivity depending on the structure of the fluoran compounds.

For example, the fluoran compounds of the general formula (I) wherein $R_1$ is $(C_2H_5)_2N-$ or $((CH_3)_2CHCH_2CH_2)(C_2H_5)N-$ can not form any addition produce with acetone nor with methylethyl ketone.

The structure of the addition compound of this invention is not clear, but it is considered that the fluoran compound and ketone are bound by a weak chemical force such as found in the formation of clathrate compound, for example, by the force such as hydrogen bond or van der Waals force. These addition compound dissociates into the original fluoran compound and ketone by heating to melt or by heating in a solvent such as butanol or o-dichlorobenzene.

Figure 1:
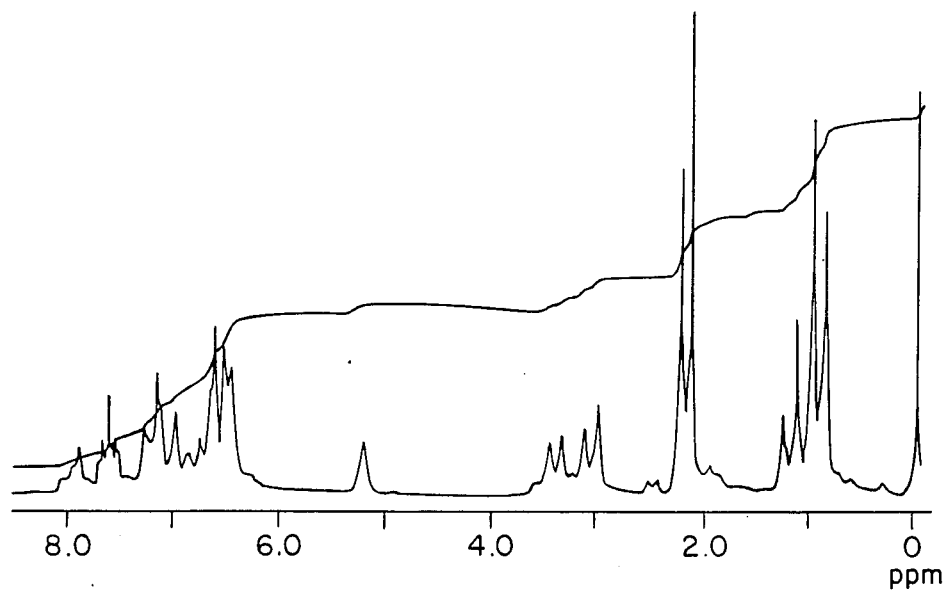
FIG. 1 shows a nuclear magnetic resonance (NMR) spectrum of the addition compound of this invention.
Figure 2:
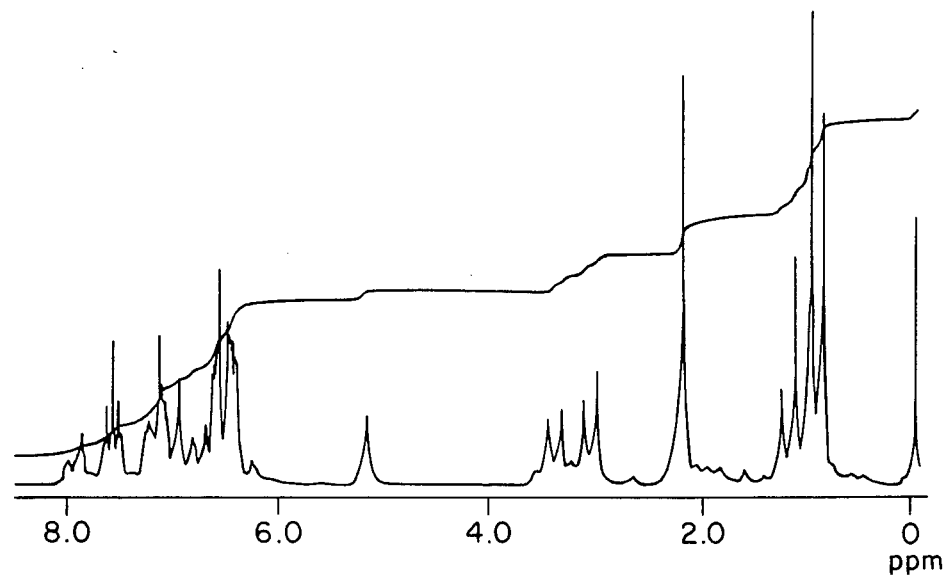
FIG. 2 shows a nuclear magnetic resonance (NMR) spectrum of the starting fluoran compound.

FIG. 1 shows a NMR spectrum of the addition compound A-1, and FIG. 2 shows a NMR spectrum of the fluoran compound A. In FIG. 1, a signal of hydrogen in methyl group of acetone appears at (delta) 2.18 ppm, and its integrated intensity is equal to the integrated intensity of the signal of hydrogen of methyl radical at 6-position of the fluoran compound found at (delta) 2.22 ppm. Therefore, it is understood that one molecule of ketone is added to 2 molecules of the fluoran compound in this addition compound.

In the NMR spectrum, $CD_3Cl$ is used as a solvent and TMS is used as a standard substance.

Table 2 shows that the heat sensitive recording paper made from the addition compound of the this invention has extremely high color developability by heat as compared to the one made using the fluoran compound without addition of ketone. In table 2, the higher numerals indicate the higher density of the resulting color. The color developers used in these experiments are 2,2-bis(p-hydrophenyl)propane (bisphenol A) and benzyl p-hydroxybenzoate (P-HBAB).

The method of production of heat sensitive recording paper using the addition compound of the this invention is similar to that using the known color developing dye, for example, as disclosed in Japanese Patent Publications (after examination) Nos. Tokkosho 39-27579 (1964), Tokkosho 43-4160 (1968) and Tokkosho 45-14039 (1970), and Japanese Patent Publication (before examination) No. Tokkaisho 59-7087 (1984). In the other words, the heat sensitive recording paper having excellent color developability can be produced by dispersing finely divided particles of the addition compound of the this invention and finely divided particles of a color developer into an aqueous solution of a water soluble binding agent to form the suspension, applying the suspension to the surface of paper to form a heat sensitive layer, and drying. Further if a sensitizer is added to the suspension, the heat sensitive recording paper having extremely high sensitivity can be produced. The suspension can contain further a filler, a dispersing agent, a color stabilizing agent, an anti-oxidant, a desensitizer, an anti-tack agent, an anti-foaming agent, a light stabilizer, a fluoresent brightening agent and etc.

Other than the aforementioned bisphenol A and P-HBAB, there may be listed as a color developer, bisphenol compounds such as
4,4'-secondary-butylidene bisphenol, 4,4'-cyclohexylidene bisphenol, 2,2'-dihydroxyldiphenyl, pentamethylene-bis(4-hydroxylbenzoate);
sulpher-containing bisphenol compounds such as 1,7-di(4-hydroxyphenylthio)-3,5-dioxaheptane;
4-hydroxybenzoicacid esters such as ethyl 4-hydroxybenzoate, propyl-4-hydroxybenzoate, isopropyl-4-hydroxybenzoate, butyl-4-hydroxybenzoate, isobutyl-4-hydroxybenzoate, chlorobenzyl-4-hydroxybenzoate, methylbenzyl-4-hydroxybenzoate, diphenylmethyl-4-hydroxybenzoate;
hydroxy sulfones such as 4-hydroxy-4'-methyldiphenylsulfone, 4-hydroxy-4-'isopropoxydiphenylsulfone, 4-hydroxy-4'-butoxydihenylsulfone;
4-hydroxyphthalic acid diesters such as dimethyl-4-hydroxyphthalate, dicyclohexyl-4-hydroxyphthalate, diphenyl-4-hydroxyphthalate;
esters of hydroxynaphtoeic acid such as 2-hydroxy-6-carboxynaphthalene;
and further hydroxyacetophenone, p-phenylphenol, benzyl-4-hydroxyphenylacetate, p-benzyphenol, hydroquinone-monobenzyl ether.

There can be mentioned, as a water soluble binding agent, polyvinyl alcohol, hydroxyethyl cellulose, carboxymethyl cellulose, salt of styrene-maleic anhydride copolymer, styrene-butadiene emulsion, vinylacetate-maleic anhydride emulsion, salt of polyacrylic acid, polyacryl amide, starchs, casein, gum arabic, and the like. But, it can not be restricted to these materials.

There can be mentioned, as a sensitizer, higher fatty acid amide, benz amide, stearic acid anilide, acetoacetic acid anilide, thioaceto anilide, dimethyl phthalate, dibenzyl terephthalate, dibenzyl isophthalate, bis(tert-butylphenols), diethers of bisphenol S such as 4,4'-dimethoxy diphenylsulfone, 4-iso-propoxyl-4'-n-butoxydiphenylsulfone, 4,4'-dibutoxy diphenylsulfone, 4,4'-di-n-(or iso-)pentyloxydiphenylsulfone; diphenyl amine, carbazole, 2,3-di-m-tolylbutane, 4,4'-dimethyl bisphenyl, di-$\beta$-naphthyl phenylenediamine.

There can be mentioned, as a filler, clay, talc, kaoline, satine white, titanium oxide, calcium carbonate, magnesium carbonate, barium sulfate, magnesium silicate, aluminium silicate, and the like.

There can be mentioned, as a dispersing agent, sulfosuccinic acid ester such as sodium dioctylsuccinate, sodium dodecylbenzenesulfonate, sodium salt of laurylalcoholsulfate ester, salt of fatty acid and the like.

There can be mentioned, as a color stabilizing agent, metal salt, preferrably zinc salt of salicylic acid derivatives and oxynaphtoeic acid derivatives, and water insoluble zinc compouns.

There can be mentioned, as an antioxidant, 2,2'-methylene-bis(4-methyl-6-tert-butylphenol), 2,2'-methylenebis(4-ethyl-6-tert-butylphenol), 4,4'-propylmethylenebis(3-methyl-6-tert-butylphenol), 4,4'-thiobis(2-tert-butyl-5-methylphenol), and the like.

There can be mentioned, as a disensitizer, alliphatic higher alcohol, polyethylene glycol, guanidine derivatives and the like.

There can be mentioned, as an anti-tack agent, stearic acid, zinc stearate, calcium stearate, carnauba wax, paraffin wax, ester wax and the like.

It should be noted that the addition compound of this invention can be used in the pressure sensitive recording paper. The method of application of the addition compound to the said use is similar to that of the general fluoran compounds, as disclosed in U.S. Pat. Nos. 2,548,365, 2,548,366, 2,800,457 and 2,800,458 and Japanese Patent Publications (before examination) Nos. Tokkaisho 58-11204 (1983) and Tokkaisho 58-139738 (1983) so that the significant pressure sensitive copying paper can be produced by such disclosed methods. The usable developer can be the conventional known developer, for example, inorganic acidic material such as acid clay, activated clay, attapulgite, bentonite, coloidal silica, aluminium silicate, magnesium silicate, zinc silicate, tin silicate, calcined kaoline, talc;

aliphaticcarboxylic acid such as oxalic acid, maleic acid, tartaric acid, citric acid, succinic acid, stearic acid;

aromatic carboxylic acid such as benzoic acid, p-tert-butylbenzoic acid, phthalic acid, gallic acid, salicylic acid, 3-isopropylsalicylic acid, 3-phenylsalicylic acid, 3-cyclohexylsalicylic acid, 3,5-di-tert-butylsalicylic acid, 3-methyl-5-benzylsalicylic acid;

3-phenyl-5-($\alpha,\alpha$-dimethylbenzyl)salicylic acid, 3,5-di-(2-methylbenzyl)salicylic acid, 2-hydroxy-1-benzyl-3-naphthoeic acid, salt of those aromatic carboxylic acid with metal such as zinc, magnesium, aluminium, titanium;

phenol resin developer such a p-phenylphenol formaline resin and p-butylphenol-acetylene resin;

the mixture of those phenol resin developer with the said metal salt of aromatic carboxylic acid and the like.

The addition compound of this invention can be used as a color former for a recording paper in a heat sensitive transfer method, a electro conductive recording paper, electronic photography using a developing agent of toner containing acidic substance, stamp ink, and an ink ribon for typewriter, other than for a heat sensitive recording paper and a pressure sensitive copying paper. The heat sensitive transfer system can utilize the inventive prdoct, for example, in the method disclosed in Japanese Patent Publication (before examination) Nos. Tokkaisho 58-212985 (1983), 58-33185 (1983) and 59-42995 (1984).

Further, the addition compound of this invention can be used in the electro conductive recording paper as disclosed in Japanese Patent Publication (before examination) Nos. Tokkaisho 48-96137 (1973), Tokkaisho 48-101935 (1973) and Tokkaisho 49-11344 (1974).

The addition compound of this invention can be used in the electro photography as disclosed in Japanese Patent Publication (before examination) Nos. Tokkaisho 52-24530 (1977) and 52-56932 (1977).

It should be noted that the addition compound of this invention can be used in the mixture with the other color formers.

The following examples illustrate the practice of the invention, but should not be interpreted for the limitation of the invention.

EXAMPLE 1

Preparation of Addition Compound A-1

30.0 G of the fluoran compound A was added to 300 ml of acetone and refluxed for 20 minutes and cooled to precipitate fine white crystals. This precipitate was filtered and dried, yielding 20.3 g of the addition compound A-1 which has a melting point at 139° C. to 141° C. The NMR spectrum thereof indicates that those crystals are the addition compound of two molecules of the fluoran compound A and one molecule of acetone.

EXAMPLE 2

Preparation of Addition Compound A-2

30.0 G of the fluoran compounds A was added to 30 ml of methylethyl ketone and heated. The fluoran compound A was completely dissolved before boiling but the reflux was continued for 10 minutes. Cooling to precipitate crystals that were filtered and dried gave 20.7 g of white crystals of addition compound A-2. The melting point thereof was 128.0° C. to 129.0° C.

EXAMPLE 3

(Application Example)

3.5 G of addition compound A-1, as a color former, 41.5 g of a 15% aqueous solution of polyvinyl alcohol (commercially available from Kurare Corporation as "Kurare 105"), 15.0 g of clay (commercially available from Engelhalt Corporation as "UW-90") and 40.0 g of pure water were put together with 150 g of glass beads (1 to 1.5 mm in size) in a polyethylene bottle of 250 ml and sealed. The bottle was mounted on a paint conditioner manufactured by Red Devil Company and shaken for five hours at the frequency of 630/minute. Then the glass beads were removed from the mixture yielding the aqueous suspension of addition compound A-1 (Suspension A).

On the other hand, 10.5 g of bisphenol A as a color developer, 41.5 g of 15% aqueous solution of polyvinyl alcohol (the above mentioned), 8.0 g of clay (the above mentioned), and 40.0 g of pure water as well as 150 g of glass beads were put in the polyethylene bottle of 250 ml and sealed. The bottle was mounted on the above mentioned paint conditioner and shaken for eight hours at the frequency of about 630/minute, and removing the glass beads to yield an aqueous suspension of bisphenol A (Suspension B).

Each 10 g of Suspensions A and B were mixed and agitated for 20 minutes to yield a coating liquid.

This coating liquid was applied to the surface of a white paper by using a wire rod No. 12, and dried for two minutes by blowing a hot air at 60° C. to produce a heat sensitive recording paper.

The applied surface of this heat sensitive recording paper was heated using a Heatgradient Tester (manufactured by Toyo Seiki Seisakusho) at 75° C., 80° C., 85° C., 90° C., 95° C., 100° C., 110° C., 120° C., and 150° C. for 5 seconds under the pressure of 1 kg/cm$^2$ to develop color, and measured the densities of resulting color on the paper surface by Macbeth reflection densitometer (filter: Ratten #106). The results were shown in Table 2.

EXAMPLES 4 TO 6

(Application Examples)

Using the addition compound A-1 or B as a color former and bisphenol A or P-HBAB as a color developer, the procedures of example 3 were repeated to produce a heat sensitive recording paper. The papers were colored and the densities of the color were measured. The results were shown in Table 2.

Comparatives 1 to 4:

Using the fluoran compounds A, B or C as a color former and bisphenol A or P -HBAB as a color developer, the procedures of example 3 were repeated to produce heat sensitive recording papers, followed by color developing, measuring of the densities of developed color. The results were shown in Table 2.

EXAMPLE 7

(Application Example)

1.0 G of addition compound A-1 was dissolved in 20 g of alkylnaphtharene at 90° C. (Liquid A).

2.0 G of gelatin (isoelectric point: 8.0) and 0.5 g of carboxymethyl cellulose were completely dissolved in 120 ml of water (Liquid B).

The liquids A and B were mixed at 50° C. to 60° C., and agitated in high speed to form emulsion and adjusted to pH 8.5 to 9.0 After the adjustment of pH, the high speed agitation was continued further for 20 minutes and pH of the emulsion was gradually reduced to pH 3.8 using diluted acetic acid. The emulsion was cooled to 5° C. to 10° C. with the continuing agitation and 6 g of formalin (37%) solution was added and further followed by continuing agitation for one hour at of 10° C. to 20° C.

Then, the emulsion was further adjusted to pH 9.0 by sodium hydroxide solution (5%). The resulting emulsion were further slowly agitated for several hours to yield the emulsion containing extremely finely divided capsuls encapsulated by gel membrane of carboxmethyl cellulose and gelatin, which contain an alkylnaphthrene solution of addition compound A-1 inside. This emulsion was coated on a surface of paper and dried to obtain a back coated sheet (BC sheet) of the pressure sensitive copying paper. On the other hand, phenol formalin resin was applied on the surface of a paper and dried to produce a front coated sheet (FC sheet) of the recording material. The coated surface of BC sheet was faced to the coated surface of FC sheet and one wrote down a letter on FC sheet from the upper surface of BC sheet under some writing pressure, and one found a clear letter in black color on the coated surface of BC sheet.

Further, when clay was used in place of phenol formalin resin for the above mentioned production of FC sheet, one found a clear letter in purple black color on the coating face of FC sheet.

EXAMPLE 8

(Application Example)

4.0 G of addition compound B (addition product of fluoran compound B and acetone) was mixed with 50.0 g of alkyldiphenylmethane (commecially available from Nisseki Chemical, as "Highsol SAS 296") and 36.0 g of diisopropyl naphtharene (commercially available from Kureha Chemical, as "KMC-113") and heated to dissolve, and agitated at 90° C. for ten minutes and cooled (Liquid A).

On the other hand, 30.0 g of a 10% aqueous solution of sulfonic acid modified polyvinyl alcohol (commercially available from Nippon Gosei Chemical Industories, as "gosenol CK-50", the average polymerization degree of about 300, the saponification value of 97% and modification degree of 10 mol.%), 15.0 g of a 10% aqueous solution of ethylene-maleicanhydride copolymer (commercially available from Monsanto Co. as "EMA-31") and 67.5 ml of water were mixed and further 5.0 g of urea and 0.5 g of resolsinol were added and dissolved, and then adjusted to pH 3.4 by using an 20% aqueous solution of sodium hydroxide (Liquid B).

The liquid A was added to the liquid B and agitated for two minutes by using a homomixer at the rotation of 9,000 rpm, to form an emulsion, and then 14.0 g of a 35% aqueous solution of formalin was further added and agitated for 3 minutes at the rotation of 9,000 rpm and then the rotation was reduced to 8,000 rpm, heating to 60° C. to 65° C. and further the agitation was continued for 60 minutes.

Upon discontinuing the agitation by a homomixer, the mixture was cooled to 40° C. and adjusted to pH 7.5 by adding a 28% ammonia aqueous solution to produce a suspension of microcapsules.

27.0 G of this suspension, 3.5 g of wheat starch, 8.5 g of 8% wheat starch solution and 34.0 g of water were mixed by a stirrer at room temperature for 30 minutes to yield a coating liquid.

This coating liquid was applied to the surface of a white paper using a wire rod No. 12 and dried by blowing a hot air at 60° C. for 3 minutes to produce a BC sheet of the pressure sensitive copying paper.

Using this BC sheet to face FC sheet as used in Example 7, the copying procedure as in Example 7 was carried out, one found a clear black letter on the surface of the FC sheet.

TABLE 1 general formula (I) (Fluoran compound)

$$R^1-\text{C}_6\text{H}_3-\text{O}-\text{C}_6\text{H}_3(\text{CH}_3)-\text{NH}-\text{C}_6\text{H}_5$$ (with spiro lactone)

general formula (II) (ketone)

$$\text{CH}_3-\text{C}(=\text{O})-R^2$$

| addition compound No. this invention | $R^1$ | $R^2$ | melting point (°C.) |
|---|---|---|---|
| A-1 | $\begin{array}{c}\text{CH}_3\\ \phantom{x}\diagdown\\ \text{CH}_3\end{array}\text{CH}-\text{CH}_2-\text{N}(\text{C}_2\text{H}_5)-$ (amino group A) | $\text{CH}_3-$ | 139–141 |
| A-2 | amino group A | $\text{C}_2\text{H}_5-$ | 128–129 |
| B | cyclohexyl-N(CH$_3$)– (amino group B) | $\text{CH}_3-$ | 133–135 |
| C | $\text{H}_3\text{C}-\text{C}_6\text{H}_4-\text{N}(\text{C}_2\text{H}_5)-$ (amino group C) | $\text{CH}_3-$ | 152–153 |
| starting material | | | |
| fluoran compound A | amino group A | — | 151–154 |
| fluoran compound B | amino group B | — | 206–208 |
| fluoran compound C | amino group C | — | 207–209 |

TABLE 2

| color former | 75 | 80 | 85 | 90 | 95 | 100 | 110 | 120 | 150 | Color developer | note |
|---|---|---|---|---|---|---|---|---|---|---|---|
| addition compound A-1 (this invention) | 0.20 | 0.23 | 0.28 | 0.40 | 0.68 | 0.87 | 1.20 | 1.30 | 1.32 | bisphenol A | example 3 |
| fluoran compound A | 0.14 | 0.14 | 0.14 | 0.15 | 0.19 | 0.24 | 0.50 | 1.06 | 1.30 | bisphenol A | comparative 1 |
| addition compound A-1 (this invention) | 0.26 | 0.51 | 0.91 | 1.13 | 1.27 | 1.32 | 1.34 | 1.36 | 1.37 | P-HBAB | example 4 |
| fluoran compound A | 0.23 | 0.37 | 0.72 | 1.06 | 1.25 | 1.32 | 1.34 | 1.36 | 1.37 | P-HBAB | comparative 2 |
| addition compound B (this invention) | 0.27 | 0.28 | 0.35 | 0.39 | 0.66 | 0.82 | 1.21 | 1.29 | 1.32 | bisphenol A | example 5 |
| fluoran compound B | 0.09 | 0.10 | 0.11 | 0.11 | 0.15 | 0.18 | 0.49 | 1.16 | 1.31 | bisphenol A | comparative 3 |
| addition compound B (this invention) | 0.68 | 0.97 | 1.16 | 1.27 | 1.32 | 1.34 | 1.38 | 1.38 | 1.38 | P-HBAB | example 6 |
| fluoran compound B | 0.12 | 0.14 | 0.27 | 0.78 | 1.17 | 1.26 | 1.32 | 1.32 | 1.32 | P-HBAB | comparative 4 |

Color developing temperature (°C.)

We claim:

11

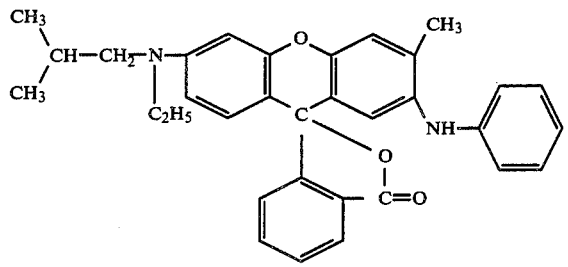

and 1 molecule of ketone selected from acetone and methylethyl ketone, which is obtainable by maintaining fluoran compound in the ketone at reflux temperature of the ketone for 20 minutes.

* * * * *

12

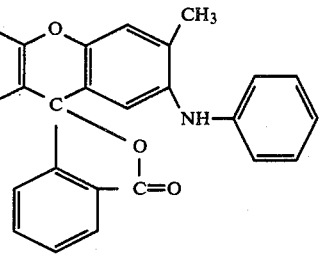

and 1 molecule of ketone selected from acetone and methylethyl ketone, which is obtainable by maintaining fluoran compound in the ketone at reflux temperature of the ketone for 20 minutes.

* * * * *

UNITED STATES PATENT AND TRADEMARK OFFICE
CERTIFICATE OF CORRECTION

PATENT NO. : 4,695,640
DATED : September 22, 1987
INVENTOR(S) : Masakichi YAHAGI et al It is certified that error appears in the above-identified patent and that said Letters Patent is hereby corrected as shown below:

IN THE CLAIMS:

Column 11, at line 1 before the formula insert:

-- 1. Crystals of fluoran compound consisting of 2 molecules of fluoran compound of --

Delete column 12.

Signed and Sealed this

Twelfth Day of January, 1988

Attest:

DONALD J. QUIGG

*Attesting Officer*  *Commissioner of Patents and Trademarks*